United States Patent [19]
Cox

[11] Patent Number: 5,540,724
[45] Date of Patent: Jul. 30, 1996

[54] CARDIAC CARDIOVERTER/DEFIBRILLATOR WITH IN VIVO IMPEDANCE ESTIMATION

[75] Inventor: Timothy J. Cox, Lake Jackson, Tex.

[73] Assignee: Intermedics, Inc., Angleton, Tex.

[21] Appl. No.: 383,465

[22] Filed: Feb. 3, 1995

[51] Int. Cl.$^6$ ............................................. A61N 1/37
[52] U.S. Cl. ................................. 607/8; 607/28
[58] Field of Search ..................... 607/5–8, 11, 28; 128/734, 908

[56] References Cited

U.S. PATENT DOCUMENTS

| | | | |
|---|---|---|---|
| 4,350,403 | 9/1994 | Stroetmann et al. | 607/8 |
| 4,771,781 | 9/1988 | Lerman | 128/908 X |
| 4,961,047 | 10/1990 | Carder | 128/908 X |
| 5,111,813 | 5/1992 | Charbonnier et al. | 128/734 |
| 5,344,430 | 9/1994 | Berg et al. | 607/8 |

FOREIGN PATENT DOCUMENTS

| | | | |
|---|---|---|---|
| 338363 | 10/1989 | European Pat. Off. | 607/28 |

Primary Examiner—William E. Kamm
Assistant Examiner—Jeffrey R. Jastrzab
Attorney, Agent, or Firm—John R. Merkling

[57] ABSTRACT

An implantable device, such as a defibrillator which may include cardioversion and pacemaker capabilities, which automatically measures the impedance of the heart prior to the delivery of a cardioverting shock. The defibrillator adjusts the voltage level on output capacitors to deliver a selected energy to the patient's heart. Insulated gate bipolar transistors, or similar devices having an inherent capacitance such that when they are turned on a small voltage gradient will exist across the transistor, are used as switches to control the application of electrical energy to the heart for therapy. When the switches are turned on, a current flows through a connected circuit path, for example through the heart and associated leads. Measurement of the current gives a measure of the impedance of the heart. An initial measurement is performed at the time of implantation of the implantable device, when the initial energy level (and output voltage) is selected. By scaling from this initial measurement to a second in vivo measurement of current, the implantable device can be programmed to adjust the voltage on or output voltage of the output capacitors.

14 Claims, 3 Drawing Sheets

5,540,724

CARDIAC CARDIOVERTER/DEFIBRILLATOR WITH IN VIVO IMPEDANCE ESTIMATION

FIELD OF MY INVENTION

My invention is directed towards an implantable biomedical device such as a cardiac pacemaker or a cardioverter-defibrillator, incorporating an output regulating circuit for controlling the energy applied to the heart. The circuit opens insulated gate bipolar transistors or similar switching devices connected through leads to the heart. An inherent capacitance of the switching devices allows a current to flow through the leads and intervening body pads of the patient. The current is measured and used to scale the voltage on an output capacitor so that when the output capacitor is discharged through the heart, the energy delivered will be substantially the same as a preselected energy.

BACKGROUND OF MY INVENTION

The basic implantable cardioverter/defibrillator or pacemaker system consists of at least one electrode attached to the heart and connected by a flexible lead to a pulse generator. This generator is a combination of a power source and the microelectronics required for the system to perform its intended function. A fixed rate pacemaker provides continuous pulses to the heart, irrespective of proper heart beating, while a demand inhibited pacemaker provides pulses only when the heart fails to deliver a natural pulse. Depending upon the various sensed events, the pacemaker stimulates the right atrium, the right ventricle, or both chambers of the heart in succession. The pacemakers in current use incorporate circuits and antennae to communicate non-invasively with external instruments called programmers. Most of today's pacemakers are of the demand inhibited type, hermetically sealed, and programmable. Implantable cardioverters/defibrillators add the capability of correcting dangerous arrhythmias and fibrillation by selected stimulation patterns or high energy shocks. High energy shocks are used primarily to correct life-threatening fibrillations by essentially stopping the heart and allowing an appropriate rhythm to re-establish itself.

To achieve reversion to an organized rhythm, it is generally believed that the heart should receive an effective amount of electrical energy, equal to or exceeding a threshold energy. The threshold energy may vary from patient to patient. Consequently, a physician will customarily perform certain tests when implanting a defibrillator and will select an energy level for defibrillating shocks. Implantable defibrillators are configured to deliver electrical energy by controlling the voltage on or applied from output capacitors. The energy delivered to the heart is often set on the assumption that the impedance of the electrical path including the leads and the heart is fixed.

Unfortunately, a fixed impedance is not assured at implant and its characteristics over time cannot be guaranteed. There may be changes in the heart itself, or in surrounding tissue. The position of the leads may change, or the body may react to the presence of the leads as foreign bodies. If the impedance of the electrical path changes, the amount of electrical energy delivered to the heart will also change, and may unintentionally fall below the threshold energy or the energy level prescribed by the attending physician.

SUMMARY OF MY INVENTION

I have invented an implantable defibrillator, which may include cardioversion and pacemaker capabilities, which automatically measures the impedance of the heart prior to the delivery of a cardioverting shock. The device of my invention adjusts the voltage level on output capacitors to deliver a selected energy to the patient's heart. Insulated gate bipolar transistors, or similar devices, are used as switches to control the application of electrical energy to the heart for therapy. These transistors have an inherent capacitance, such that when they are turned on a small potential difference will be produced across the transistor. As this potential difference increases, a current is caused to flow through a connected circuit path, for example through the heart and associated leads. Measurement of the current gives a measure of the impedance of the heart. In my preferred embodiment, an initial measurement is performed at the time of implantation of the implantable device, in order to set output voltage corresponding to the energy selected. By scaling from this initial measurement to a second in vivo measurement of current, the implantable device can be programmed to adjust the voltage on or output voltage of the output capacitors.

With the foregoing in mind, it is a principal object of my invention to provide an implantable medical device capable of providing a consistent energy therapy to at least a part of a patient's body.

A further object of my invention is to provide an implantable medical device which can detect changes in impedance and control the voltage of therapy delivered to at least a part of a patient's body in response to said detected changes.

It is another object of my invention to provide a medical device which can sample in vivo impedance of a portion of a patient's body without a dedicated impedance signal.

I will now describe my preferred embodiment of my invention, in connection with the accompanying drawings.

DESCRIPTION OF MY PREFERRED INVENTION

Figure 1:
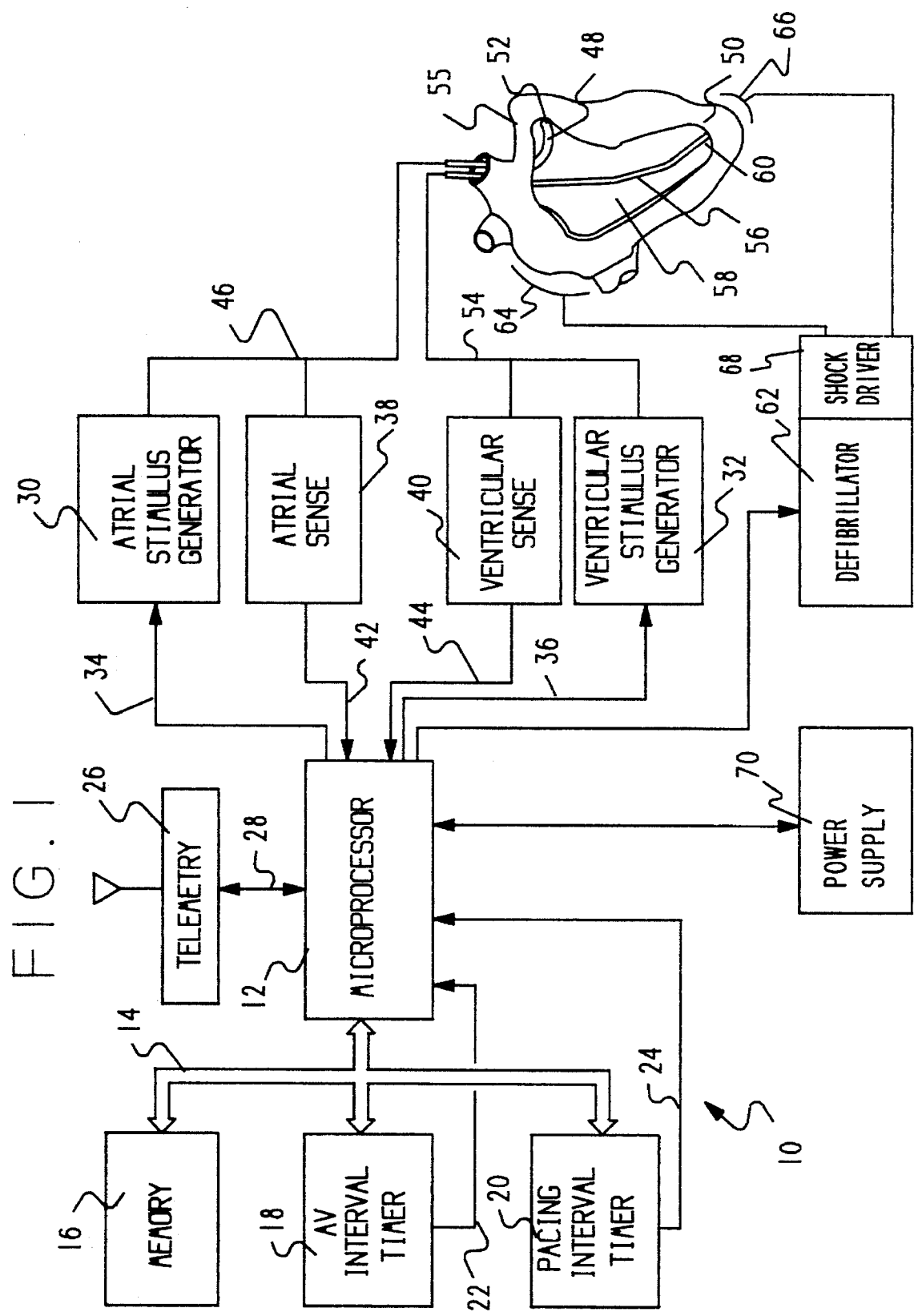
FIG. 1 is a block diagram of an implantable pacemaker/defibrillator.

FIG. 1 is a block diagram illustrating a rate adaptive pacemaker/defibrillator 10 according to my invention. A microprocessor 12 preferably provides pacemaker control and computational facilities. It will be appreciated that other forms of circuitry, such as analog or discrete digital circuitry can be used in place of microprocessor 12. However, a microprocessor is preferred for its miniature size and its flexibility, both of which are of critical importance in the implantable systems in which it is envisioned the invention will find use. A particularly energy efficient microprocessor which is designed specifically for use with implantable medical devices is fully described in Gordon, et al, U.S. Pat. No. 4,404,972, which is also assigned to my assignee and the disclosure thereof is incorporated herein by reference.

The microprocessor 12 has input/output ports connected in a conventional manner via bidirectional bus 14 to a memory 16, an A-V interval timer 18, and a pacing interval timer 20. In addition, the A-V interval timer 18 and pacing interval timer 20 each has an output connected individually to a corresponding input port of the microprocessor 12 by lines 22 and 24 respectively.

Memory 16 preferably includes both ROM and RAM. The microprocessor 12 may also contain additional ROM and RAM as described in the Gordon, et al. U.S. Pat. No. 4,404,972. The pacemaker operating routine is stored in ROM. The RAM stores various programmable parameters and variables.

The A-V and pacing interval timers 18 and 20 may be external to the microprocessor 12, as illustrated, or internal thereto, as described in the Gordon, et al. U.S. Pat. No. 4,404,972. The timers 18, 20 are suitable conventional up or down counters of the type that are initially loaded with a count value and count up to or down from the value and output a roll-over bit upon completing the programmed count. The initial count value is loaded into the timers 18, 20 on bus 14 and the respective roll-over bits are output to the microprocessor 12 on lines 22, 24.

The microprocessor 12 preferably also has an input/output port connected to a telemetry interface 26 by line 28. The pacemaker when implanted is thus able to receive pacing, arrhythmia therapy, and rate control parameters from an external programmer and send data to an external receiver if desired. Many suitable telemetry systems are known to those skilled in the art. One such system and encoding arrangement is described in Armstrong and Cox, U.S. Pat. No. 5,383,912 which is also assigned to my assignee. That description is incorporated herein by reference.

The microprocessor 12 output ports are connected to inputs of an atrial stimulus pulse generator 30 and a ventricle stimulus pulse generator 32 by control lines 34 and 36 respectively. The microprocessor 12 transmits pulse parameter data, such as amplitude and width, as well as enable/disable and pulse initiation codes to the generators 30, 32 on the respective control lines.

The microprocessor 12 also has input ports connected to outputs of an atrial sense amplifier 38 and a ventricular sense amplifier 40 by lines 42 and 44 respectively. The atrial and ventricular sense amplifiers 38, 40 detect occurrences of P-waves and R-waves. The atrial sense amplifier 30 outputs a signal on line 42 to the microprocessor 12 when it detects a P-wave. This signal is latched to the microprocessor 12 input port by a conventional latch (not shown). The ventricular sense amplifier 40 outputs a signal on line 44 to the microprocessor 12 when it detects an R-wave. This signal is also latched to the microprocessor 12 input port by a conventional latch (not shown).

The input of the atrial sense amplifier 38 and the output of the atrial stimulus pulse generator 30 are connected to a first conductor 46, which passes through a conventional first lead 48. Lead 48 is inserted into a patient's heart 50 intravenously or in any other suitable manner. The lead 48 has an electrically conductive pacing/sensing tip 52 or tip and ring at its distal end which is electrically connected to the conductor 46. The pacing/sensing tip 52 is preferably lodged in the right atrium 55.

The input of the ventricular sense amplifier 40 and the output of the ventricular stimulus pulse generator 32 are connected to a second conductor 54. The second conductor 54 passes through a conventional second lead 56 which is inserted intravenously or otherwise in the right ventricle 58 of the heart 50. The second lead 56 has an electrically conductive pacing/sensing tip 60 or tip and ring at its distal end. The pacing/sensing tip 60 is electrically connected to the conductor 54. The pacing/sensing tip 60 is preferably lodged on the wall of the right ventricle 58.

The conductors 46, 54 conduct the stimulus pulses generated by the atrial and ventricular stimulus pulse generators 30, 32 respectively, to the pacing/sensing tips 52, 60. The pacing/sensing tips 52, 60 and corresponding conductors 46, 54 also conduct cardiac electrical signals sensed in the right atrium and right ventricle to the atrial and ventricular amplifiers, 38, 40 respectively. The sense amplifiers 38, 40 enhance the electrical signals. In the preferred embodiments of my invention, the amplifiers 38, 40 have an automatic gain control feature, as described in U.S. Pat. 4,903,699 to Baker, et al. That application is assigned to the same assignee as my present invention, and the disclosure thereof is incorporated herein by reference.

The implantable cardiac stimulator 10 also has a defibrillator circuit 62. If fibrillation is detected through the atrial or ventricular sense amplifiers 38, 40, a high energy shock can be delivered through defibrillation leads and electrodes 64, 66. Detection algorithms for detection of tachycardias and fibrillation are described in Pless, et al., U.S. Pat. No. 4,880,005, incorporated herein by reference. Although patch-type electrodes are suggested by the drawing, endocardial electrodes for defibrillation are also known. The shock is controlled by a shock driver circuit 68, which will be more particularly described hereafter. All of the aforementioned components are powered by a power supply 70. The power supply 70 may comprise either standard or rechargeable batteries or both, which may be dedicated to the operation of different parts of the stimulator 10.

Figure 2:
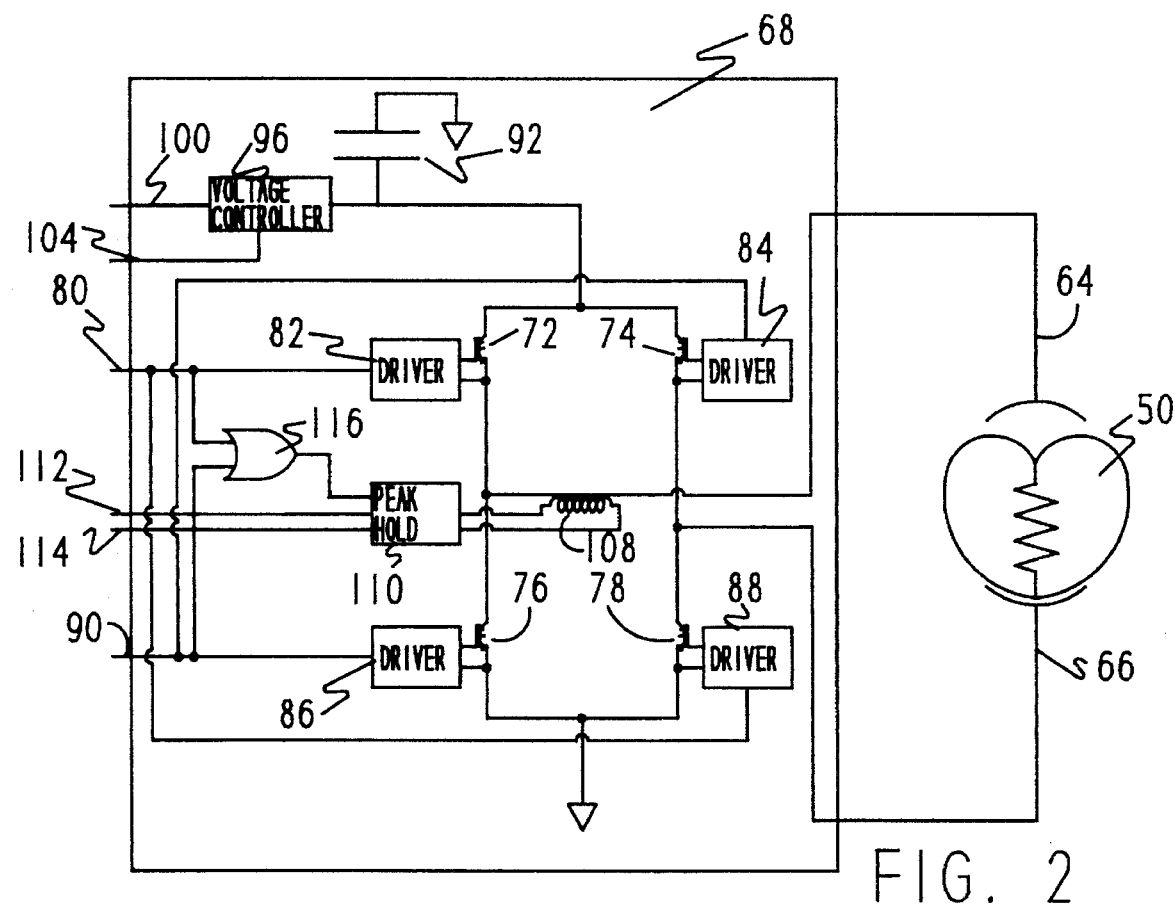
FIG. 2 is a block diagram of an output circuit for use in the defibrillator of FIG. 1.

In the preferred embodiment of my invention, I consider it desirable to produce multi-phasic shocks for defibrillation through the shock driver 68. Circuitry particularly well adapted for producing such wave forms is described in detail in U.S. Pat. No. 4,800,883 to Winstrom, the disclosure of which is incorporated herein by reference. Circuitry for the shock driver 68 is shown with greater particularity in FIG. 2. FIG. 2 illustrates the shock driver 68 connected to the patient's heart 50 through the leads and electrodes 64, 66. To produce a biphasic wave form, a bank of four insulated gate bipolar transistor (IGBT) switches 72, 74, 76, 78 are employed. It will be understood, however, that my invention can be employed with monophasic pulse generators and with pulse generators incorporating multiphasic stimulation. In addition to IGBT's, other electronic devices could be employed for the switches 72, 74, 76, 78. What is important for my invention, however, is that the switches 72, 74, 76, 78 have an inherent capacitance. By inherent capacitance, I mean that when the switches are closed, completing a circuit, a certain amount of charge flows through the switches which will cause a small current to flow through the circuit, including, in this case, the heart 50, without the application of an additional signal. The switches 72, 74, 76, 78 are controlled by drivers 82, 84, 86, 88 respectively. The drivers 82, 84, 86, 88 are controlled by command pulses from the microprocessor 12 through control lines 80 and 90, as will be more particularly described below. The energy to produce biphasic defibrillating shocks is supplied from power capacitor 92. Power capacitor 92 is connected to switches 72 and 74, and current therefrom returns via switches 76 or 78. The first lead 64 is connected between switches 72 and 76 while the second lead 66 is connected between switches 74 and 78.

The amount of energy delivered to the heart is dependant upon the voltage on the power capacitor. The voltage appearing on the capacitor 92 is controlled by voltage controller 96 which is connected to a source of power such as the battery or power supply 70 through line 100. The voltage controller 96 is controlled through a line 104 from the microprocessor 12. This configuration is described in more detail in the Winstrom patent mentioned above. Winstrom does not, however, describe the dynamic voltage control system, based on measured impedance, which is described herein. In the configuration shown, to produce a unidirectional current pulse through the heart 50, the microprocessor 12 issues a command along line 80 to drivers 82 and 88, closing switches 72 and 78. Both before and after the command, all switches are normally opened. To produce an opposite current, the microprocessor 12 issues a command on line 90, closing switches 84 and 86 and directing the current flow in the opposite direction through the heart 50.

It is important, however, that the energy delivered through heart 50 exceed a threshold value determined by the physician. In the apparatus described by Winstrom, the energy is approximately controlled by controlling the voltage on the power capacitor 92. However, if there is a change in the impedance of the system comprising leads and electrodes 64, 66 and the head 50 after implantation of the device, the energy delivered will vary, even though the initial voltages are constant. It is important, therefore, to check the impedance of the system before delivering a shock to the heart 50 so that the voltage on the power capacitor 92 can be dynamically adjusted to control the energy delivered to the heart. To accomplish this, I have provided a sensing circuit. The sensing circuit comprises an induction coil 108 which is placed adjacent to one of the conductors connected through a lead to an electrode, such as lead and electrode 64, adjacent heart 50. The induction coil 108 preferably comprises a plurality of coils surrounding the single strand of the conductor. An exemplary current sensor coil is available from Jaycor of San Diego, Calif., referred to as an Ultra Miniature Current Sensor. I prefer, however, to custom fabricate a suitable coil by passing several turns of conductive material around the lead supported by a magnetic core. The induction coil 108 is connected to a peak hold circuit 110, more particularly described below, whose function is to capture the highest current detected through the induction coil 108 during a sampling period. The peak hold circuit 110 is enabled by a command from the microprocessor 12 along a line 112 and produces an output to the microprocessor along another line 114. The output may be translated into digital information either in a specialized circuit in the microprocessor or in a dedicated analog-to-digital converter (not shown). In addition, the peak hold circuit 110 is disabled and protected whenever a shock is being delivered to the heart. An OR gate 116 is connected to both lines 80 and 90 and produces a logical control output to the peak hold circuit whenever either a negative pulse or a positive pulse is initiated.

Figure 3:
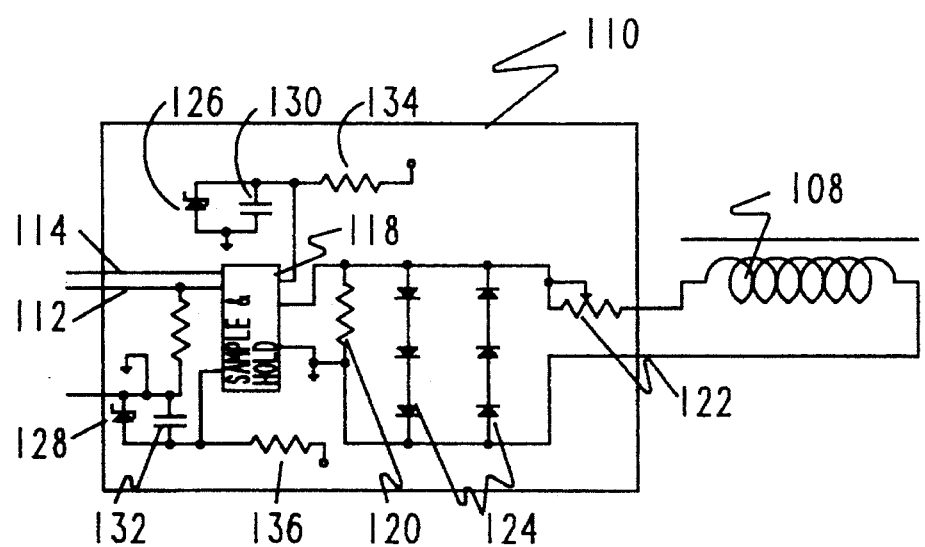
FIG. 3 is a diagram of a peak hold circuit for use in the output circuit of FIG. 2.

As shown in FIG. 3, the peak hold circuit 110 may be structured around a conventional sample and hold circuit 118, for example, an AD783 device available from Analog Devices. The induction coil 108 is connected to the sample and hold circuit 118 in parallel with a damping resistor 120 allowing the transient phenomenon of interest to be detected without unnecessary perturbations or distortion. A trimming resistor 122 may be provided for scale adjustment to match the output of the induction coil 108 to the input of the sample and hold circuit 118. A bank of diodes 124 connected in parallel to the induction coil 108 acts as a surge protector. This is important because the high voltage shocks applied as therapy will also induce current in the induction coil, which current will be much greater than the currents to be captured by the sample and hold circuit. It is necessary, therefore, to protect the circuit 118 from the high currents generated in connection with shock therapy. The circuit 118 is connected through line 112 to an analog-to-digital converter (not shown) and then to the microprocessor 12 which times the sampling of the current based on the microprocessor's control of the switches 72, 74, 76, 78. The output of the circuit 118 is carried on line 114, as explained above. In the particular embodiment shown, appropriate operating voltages are supplied to the sample and hold circuit through zener diodes 126, 128, decoupling capacitors 130, 132 and biasing resistors 134, 136.

In order to adjust the voltage level on the power capacitor 92, before the capacitor is charged, at least two of the switches 72, 74, 76, 78, for example switches 72 and 78, are closed by the microprocessor 12 by commands along lines 80 or 90. However, at the time the command is issued, there is no charge on the power capacitor 92. A residual inherent capacitance of the switches 72, 78 produces a current through the leads, electrodes 64, 66 and the heart 50. Although the test may be performed by completing a circuit through the heart by closing only two switches (72, 78), it may be desired to subsequently perform an additional redundant test by closing the other two switches 74, 76. The two measurements thus obtained could be combined for additional accuracy. Of course, if a monophasic system is employed, only a single switch might be used without departing from the essential features of my invention.

The inherent capacitance of the four switches 72, 74, 76, 78 is dependent on the characteristics of the four individual devices employed for the switches, but will remain relatively constant during the life of the implantable device. Consequently, the device can be calibrated at implantation. During implantation, it is customary to defibrillate the heart several times to determine the threshold energies. Before the first defibrillating shock, a known resistor is connected between the electrodes in stead of the patient's heart. When the physician has initiated a calibration request, the microprocessor will have associated therewith a current caused by the inherent capacitance of a pair of the switches 72, 74, 76 and 78 which is detected by the induction coil 108, which I will call a calibrated or calibration current. After implantation, whenever the device 10 is called upon to deliver a shock to the heart, the microprocessor 12 would initiate the test for the impedance by closing a pair of switches, for example switches 72, 78, for a short time and would detect the current through the induction coil 108. The peak detected current would then be compared with the stored calibration current and the voltage to be stored on the power capacitor 92 would be scaled accordingly in a direct ratio or other appropriate function. Using the newly computed value for the voltage on the power capacitor 92, the microprocessor 12 would then initiate charging of the capacitor 92 as controlled by the voltage controller 96. When the shock is delivered to the heart 50, the energy delivered will be consistent with that set by the physician.

Figure 4:
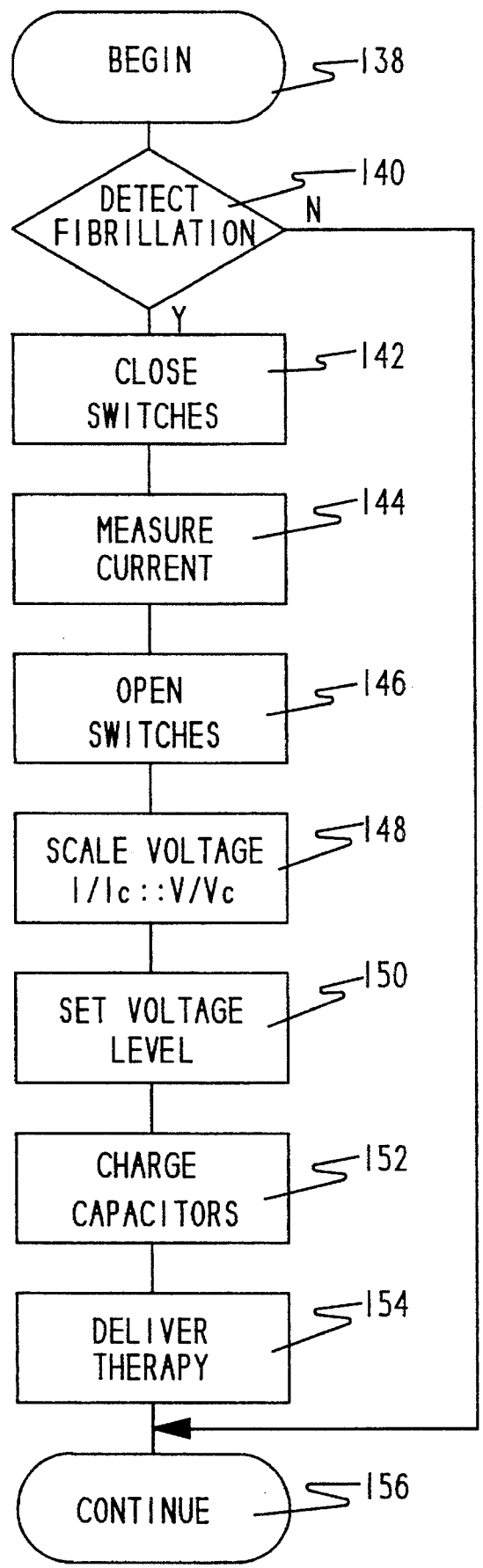
FIG. 4 is a flow chart of the logical sequence of control by the microprocessor.

This logical sequence of control by the microprocessor 12 is illustrated diagrammatically in FIG. 4. During the processing of the software controlling the device, the microprocessor would begin 138 a subroutine to deliver shock therapy to the heart. An algorithm 140 would be implemented to detect fibrillation. Various algorithms to detect fibrillation or other conditions in the heart are known, for example, those described by Pless, et al., supra. If fibrillation is not detected, the microprocessor 12 would not deliver a shock therapy. If, however, a shock therapy was determined to be necessary, the microprocessor closes 142 the switches such as switches 72, 78. The current induced in the induction coil 108 and held by the peak hold circuit 110 would be measured 144. The microprocessor 12 opens 146 the switches and scales 148 the voltage to be placed on the power capacitor 92 by the ratio of the currently detected current to a calibration current, determined during implantation, and the ratio of a voltage to be placed on the power capacitor to a calibration voltage, determined during implantation. The microprocessor 12 then sets 150 the new voltage level and directs the charging 152 of the power capacitor 92 to the appropriate voltage. When the capacitor 92 is charged, the device 10 delivers 154 a therapy to the heart. The microprocessor 12 then continues 156 with other program instructions.

While a preferred embodiment of my invention has been described above, it will be apparent to those skilled in the art from consideration of the disclosure herein that various modifications could be implemented without departing from the principles of my invention. Accordingly, it is intended that the scope of my invention be limited only by the appended claims.

I claim as my invention:

1. An implantable medical device comprising means for producing a therapeutic electrical stimulation, said means for producing a therapeutic electrical stimulation including at least one electrical switch having an inherent capacitance, means coupled to said stimulation producing means through said at least one electrical switch for communicating said stimulation to a portion of a patient's body, means in electrical communication with said stimulation producing means for controlling a magnitude of said stimulation, means for detecting an impedance of at least said portion of said patient's body by closing said switch when said stimulation is not communicated to said patient's body to discharge said switch through said portion of said patient's body and means for detecting a current produced by the discharge of said switch, and means responsive to said impedance detecting means for adjusting said magnitude controlling means to maintain said stimulation at a pre-selected energy.

2. The implantable medical device according to claim 1 wherein said means for detecting said impedance further comprises means in electrical communication with said means for communicating said stimulation for sensing electrical current in said means for communicating said stimulation.

3. The implantable medical device according to claim 2 wherein said means for detecting said impedance further comprises means in electrical communication with said current sensing means for sampling said current.

4. The implantable medical device according to claim 3 wherein said current sampling means comprises means for sampling a peak current during a selected interval of time.

5. The implantable medical device according to claim 4 wherein said means for producing a therapeutic stimulation further comprises means for producing defibrillating shocks.

6. The implantable medical device according to claim 4 wherein said means for producing a therapeutic stimulation comprises means for producing pacing pulses.

7. The implantable medical device according to claim 4 further comprising means for storing a calibration value of said current and means for comparing a present value of said current to said calibration value and wherein said means for controlling said magnitude of said stimulation includes means for scaling said magnitude as a function of said calibration value and said present value.

8. The implantable medical device according to claim 7 wherein said magnitude of said stimulation is a voltage.

9. An implantable medical device comprising means for producing a therapeutic electrical stimulation, said means for producing a therapeutic electrical stimulation having at least one electrical switch having an inherent capacitance, means coupled to said stimulation producing means for communicating said stimulation to a portion of a patient's body, means in electrical communication with said stimulation producing means for controlling a magnitude of said stimulation, means for detecting an impedance of at least said portion of said patient's body, said means for detecting an impedance having means for controlling said at least one electrical switch when said stimulation is not communicated to said patient's body, means in electrical communication with said means for communicating said stimulation for sensing electrical current in said means for communicating said stimulation, and means in electrical communication with said current sensing means for sampling a peak current during a selected interval of time, means for storing a calibration value of said peak current and means for comparing a present value of said current to said calibration value and means responsive to said impedance detecting means for adjusting said magnitude controlling means to maintain said stimulation at a pre-selected energy, said means for adjusting including means for scaling said magnitude as a function of said calibration value and said present value.

10. The implantable medical device according to claim 9 wherein said magnitude of said stimulation is a voltage.

11. An implantable medical device comprising means for producing a therapeutic electrical stimulation, means coupled to said stimulation producing means for communicating said stimulation to a portion of a patient's body, means in electrical communication with said stimulation producing means for controlling a magnitude of said stimulation, means for detecting an impedance of at least said portion of said patient's body, said impedance detecting means having means for sampling a current in said means for communicating said stimulation, means for storing a calibration value of said current, means for comparing a present value of said current to said calibration value and means responsive to said impedance detecting means for scaling said magnitude of said stimulation as a function of said calibration value and said present value to deliver a pre-selected energy.

12. The implantable medical device according to claim 11 wherein said means for producing a therapeutic stimulation further comprises means for producing defibrillating shocks.

13. The implantable medical device according to claim 11 wherein said means for producing a therapeutic stimulation comprises means for producing pacing pulses.

14. The implantable medical device according to claim 11 wherein said magnitude of said stimulation is a voltage.

* * * * *